US009637692B2

(12) United States Patent
Nagayasu et al.

(10) Patent No.: US 9,637,692 B2
(45) Date of Patent: May 2, 2017

(54) HYDROISOMERIZATION CATALYST, PROCESS FOR PRODUCING THE SAME, METHOD OF DEWAXING HYDROCARBON OIL, PROCESS FOR PRODUCING HYDROCARBON, AND PROCESS FOR PRODUCING LUBE BASE OIL

(75) Inventors: Yoshiyuki Nagayasu, Tokyo (JP); Kazuaki Hayasaka, Tokyo (JP); Hideki Ono, Tokyo (JP); Takaya Matsumoto, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 964 days.

(21) Appl. No.: 13/636,182

(22) PCT Filed: Mar. 24, 2011

(86) PCT No.: PCT/JP2011/057212
§ 371 (c)(1),
(2), (4) Date: Sep. 20, 2012

(87) PCT Pub. No.: WO2011/122446
PCT Pub. Date: Oct. 6, 2011

(65) Prior Publication Data
US 2013/0008827 A1    Jan. 10, 2013

(30) Foreign Application Priority Data

Mar. 29, 2010   (JP) .................. 2010-075410

(51) Int. Cl.
| | | |
|---|---|---|
| *B01J 29/06* | (2006.01) | |
| *C10G 45/00* | (2006.01) | |
| *C07C 5/27* | (2006.01) | |
| *C10G 45/64* | (2006.01) | |
| *C10G 45/62* | (2006.01) | |
| *C10G 65/04* | (2006.01) | |
| *B01J 29/76* | (2006.01) | |
| *B01J 29/78* | (2006.01) | |
| *B01J 29/74* | (2006.01) | |
| *B01J 37/02* | (2006.01) | |
| *B01J 37/18* | (2006.01) | |
| *B01J 37/30* | (2006.01) | |
| *B01J 37/00* | (2006.01) | |

(52) U.S. Cl.
CPC .......... *C10G 45/64* (2013.01); *B01J 29/7461* (2013.01); *B01J 29/7484* (2013.01); *B01J 29/7492* (2013.01); *B01J 29/7661* (2013.01); *B01J 29/7684* (2013.01); *B01J 29/7692* (2013.01); *B01J 29/7861* (2013.01); *B01J 29/7884* (2013.01); *B01J 29/7892* (2013.01); *B01J 37/0201* (2013.01); *B01J 37/18* (2013.01); *B01J 37/30* (2013.01); *C10G 45/62* (2013.01); *C10G 65/043* (2013.01); *B01J 37/0009* (2013.01); *B01J 2229/20* (2013.01); *B01J 2229/42* (2013.01); *C07C 5/2708* (2013.01); *C07C 5/2775* (2013.01); *C10G 2300/107* (2013.01); *C10G 2300/1022* (2013.01); *C10G 2300/1074* (2013.01); *C10G 2300/1077* (2013.01); *C10G 2300/1081* (2013.01); *C10G 2300/30* (2013.01); *C10G 2300/70* (2013.01); *C10G 2400/10* (2013.01)

(58) Field of Classification Search
CPC ...... C10G 45/64; C10G 45/62; C10G 65/043; C10G 2300/1077; C10G 2300/70; C10G 2300/107; C10G 2300/1081; C10G 2300/1074; C10G 2300/1022; C10G 2400/10; C07C 5/2775; C07C 5/2708
USPC ........... 502/66, 74, 77; 208/64, 65, 95, 100, 208/104, 141, 135, 136, 137, 138; 585/734, 738, 739
See application file for complete search history.

(56) References Cited

U.S. PATENT DOCUMENTS

| | | | |
|---|---|---|---|
| 4,490,342 A | 12/1984 | Valyocsik | |
| 4,640,829 A * | 2/1987 | Rubin ................. | B01J 29/7023 423/277 |

(Continued)

FOREIGN PATENT DOCUMENTS

| | | |
|---|---|---|
| CN | 101365667 | 2/2009 |
| CN | 101679141 | 3/2010 |

(Continued)

OTHER PUBLICATIONS

International Search Report issued with respect to PCT/JP2011/057212, mailed Jul. 5, 2011.

(Continued)

*Primary Examiner* — Elizabeth Wood
(74) *Attorney, Agent, or Firm* — Greenblum & Bernstein, P.L.C.

(57) ABSTRACT

The hydroisomerization catalyst of the present invention is a catalyst used for hydroisomerization of a hydrocarbon, including a support including a calcined zeolite modified with at least one metal selected from the group consisting of Na, K, Cs, Mg, Ca, Ba, and K, and having a thermal history that includes heating at 350° C. or more, and at least one inorganic oxide selected from the group consisting of alumina, silica, titania, boria, zirconia, magnesia, ceria, zinc oxide, phosphorus oxide, and a composite oxide containing a combination of at least two or more of these oxides; and at least one metal supported on the support and selected from the group consisting of elements belonging to Groups 8 to 10 of the periodic table, molybdenum and tungsten.

11 Claims, 1 Drawing Sheet

(56) References Cited

U.S. PATENT DOCUMENTS

| | | | |
|---|---|---|---|
| 4,683,214 A * | 7/1987 | Angevine | B01J 29/068 |
| | | | 502/64 |
| 5,246,566 A | 9/1993 | Miller et al. | |
| 5,282,958 A | 2/1994 | Santilli et al. | |
| 7,662,273 B2 | 2/2010 | Murphy et al. | |
| 7,902,413 B2 | 3/2011 | Stevenson et al. | |
| 8,758,596 B2 * | 6/2014 | Hayasaka | B01J 29/7261 |
| | | | 208/133 |
| 2003/0168379 A1 | 9/2003 | Degnan et al. | |
| 2004/0186006 A1 | 9/2004 | Biscardi et al. | |
| 2006/0229193 A1 * | 10/2006 | Biscardi | B01J 29/74 |
| | | | 502/60 |
| 2006/0264318 A1 * | 11/2006 | Shan | B01J 21/06 |
| | | | 502/60 |
| 2008/0083657 A1 | 4/2008 | Zones et al. | |
| 2008/0255398 A1 | 10/2008 | Stevenson et al. | |
| 2009/0071874 A1 | 3/2009 | Shakun et al. | |
| 2010/0181229 A1 * | 7/2010 | Hayasaka | B01J 29/064 |
| | | | 208/28 |
| 2011/0042267 A1 | 2/2011 | Hayasaka et al. | |
| 2011/0270010 A1 | 11/2011 | Hayasaka et al. | |

FOREIGN PATENT DOCUMENTS

| | | |
|---|---|---|
| JP | 2004-535479 | 11/2004 |
| JP | 2006-523136 | 10/2006 |
| JP | 2008-512512 | 4/2008 |
| RU | 2009 116 476 | 11/2010 |
| TW | 200950883 | 12/2009 |
| WO | 2007/070521 | 6/2007 |
| WO | 2009/001572 | 12/2008 |
| WO | 2009/099111 | 8/2009 |
| WO | 2010/074215 | 7/2010 |
| WO | 2011/001914 | 1/2011 |

OTHER PUBLICATIONS

English-language translation of International Preliminary Report on Patentability issued with resepct to PCT/JP2011/057212, mailed Nov. 1, 2012.

Huybrechts et al., "Bifunctional catalytic isomerization of decane over MTT-type aluminosilicate zeolite crystals with siliceous rim", Journal of Catalysis, vol. 239, Apr. 25, 2006 (available online Mar. 24, 2006), pp. 451-459.

Hayasaka et al., "Formation of ZSM-22 Zeolite Catalytic Particles by Fusion of Elementary Nanorods", Chemistry A European Journal, vol. 13, Iss. 36, Dec. 17, 2007, pp. 10070-10077.

European Search Report issued with respect to Application No. 11762677.0, dated Feb. 14, 2017.

* cited by examiner

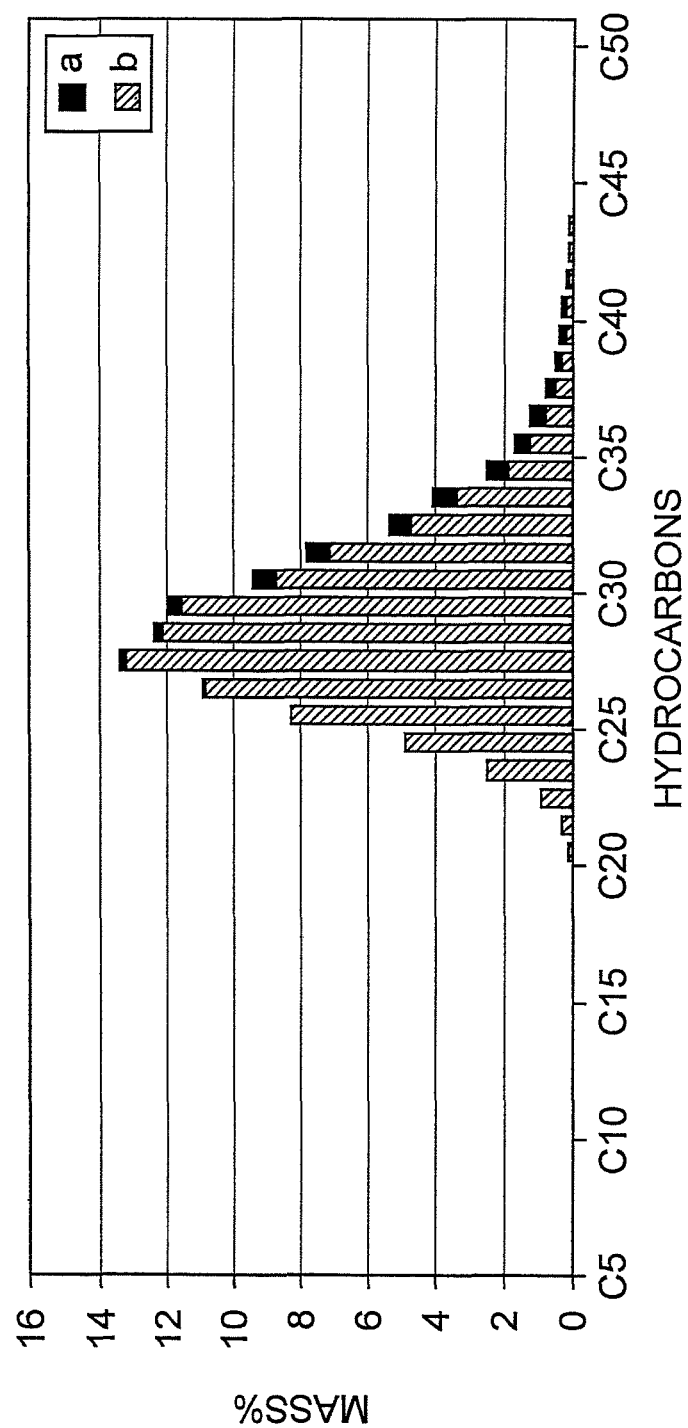

HYDROISOMERIZATION CATALYST, PROCESS FOR PRODUCING THE SAME, METHOD OF DEWAXING HYDROCARBON OIL, PROCESS FOR PRODUCING HYDROCARBON, AND PROCESS FOR PRODUCING LUBE BASE OIL

TECHNICAL FIELD

The present invention relates to a hydroisomerization catalyst, a process for producing the catalyst, a method of dewaxing a hydrocarbon oil, a process for producing a hydrocarbon, and a process for producing a lube base oil.

BACKGROUND ART

Among petroleum products, for example, lube oils, gas oils, jet fuels, and the like are products in which fluidity at low temperatures is regarded as important. For this reason, it is desirable that base oils used for these products be such that waxy components such as normal paraffins or slightly branched isoparaffins, which are responsible for reducing the low-temperature fluidity, have been completely or partially removed, or converted to components other than waxy components. Hydrocarbons obtained by Fischer-Tropsch synthesis (hereinafter abbreviated to "FT synthesis oils") have recently attracted attention as feedstocks for producing lube oils or fuels, because they do not contain substances of concern such as sulfur compounds; however, these hydrocarbons also contain many waxy components.

An example of a known dewaxing technique for removing waxy components from hydrocarbon oils is a method wherein waxy components are extracted using a solvent such as liquefied propane or MEK. However, this method has problems in that the operating costs are high, the types of usable feedstocks are limited, and the product yield is limited by the type of feedstock.

On the other hand, an example of a known dewaxing technique for converting waxy components in a hydrocarbon oil to non-waxy components is catalytic dewaxing in which the hydrocarbon oil is contacted, in the presence of hydrogen, with a so-called bifunctional catalyst capable of hydrogenation-dehydrogenation and isomerization, thereby isomerizing normal paraffins in the hydrocarbons to isoparaffins. Further, examples of known bifunctional catalysts used for catalytic dewaxing include catalysts containing solid acids, represented by molecular sieves made of, for example, zeolites, and metals belonging to Groups 8 to 10 or Group 6 of the periodic table; and in particular, catalysts in which these metals are supported on molecular sieves.

While catalytic dewaxing is an effective method for improving the low-temperature fluidity of hydrocarbon oils, it is necessary to sufficiently increase the normal paraffin conversion in order to obtain a fraction that is suitable as a lube base oil or fuel base oil. However, because the above-mentioned catalysts used in catalytic dewaxing are capable of both isomerization and hydrocarbon cracking, when a hydrocarbon oil is catalytic dewaxed, conversion of the hydrocarbon oil into lighter products also proceeds as the normal paraffin conversion increases, making it difficult to obtain a desired fraction in good yield. Particularly when producing a high-quality lube base oil in which a high viscosity index and low pour point are required, it is very difficult to economically obtain a desired fraction by catalytic dewaxing of a hydrocarbon oil; for this reason, synthetic base oils such as poly-alpha-olefins have been frequently used in this field.

In recent years, however, in the fields of the production of lube base oils and fuel base oils, and, in particular, in the field of the production of lube base oils, the production of Group II, Group III, and Group III+ base oils employing hydroprocessing has become increasingly popular. Under such circumstances, there is a need for a hydroisomerization catalyst having both suppressed cracking activity for hydrocarbons and high isomerization reaction activity, i.e., having excellent isomerization selectivity, for the purpose of obtaining a desired isoparaffin fraction in good yield from a hydrocarbon oil containing waxy components.

Attempts to improve the isomerization selectivity of catalysts used in catalytic dewaxing have been made in the past. For example, Patent Document 1 listed below discloses a process for producing a dewaxed lube oil, wherein a straight-chain or slightly branched hydrocarbon feedstock having 10 or more carbon atoms is contacted under isomerization conditions with a catalyst comprising a molecular sieve, such as ZSM-22, ZSM-23, or ZSM-48, having one-dimensional pores of an intermediate size and containing a metal of Group VIII or the like of the periodic table, and having a crystallite size of no more than about 0.5μ. Patent Document 2 listed below discloses a process for producing a dewaxed catalyst by modifying a zeolite such as SSZ-32 with a metal such as Ca, Cr, Mg, La, Ba, Na, Pr, Sr, K, or Nd.

It is noted that a molecular sieve that constitutes a catalyst for catalytic dewaxing is typically produced by hydrothermal synthesis in the presence of an organic template having an amino group, ammonium group, or the like, in order to construct a predetermined porous structure. The synthesized molecular sieve is then calcined in an atmosphere containing molecular oxygen at a temperature of, for example, about 550° C. or more, to thereby remove the organic template contained therein, as described in, for example, the final paragraph of the "2.1. Materials" section on page 453 of the Non-Patent Document 1 listed below. Next, the calcined molecular sieve is typically ion-exchanged into an ammonium form in an aqueous solution containing ammonium ions, as described in, for example, the "2.3. Catalytic experiments" section on page 453 of the Non-Patent Document 1. A metal components of Group 8 to 10 or the like of the periodic table is further supported on the ion-exchanged molecular sieve. The molecular sieve on which the metal component is supported is then subjected to steps such as drying, and optionally molding, and then loaded in a reactor; the molecular sieve is typically calcined in an atmosphere containing molecular oxygen at a temperature of about 400° C., and is further subjected to reduction treatment with, for example, hydrogen, at about the same temperature; consequently, the molecular sieve is provided with catalytic activity as a bifunctional catalyst.

CITATION LIST

Patent Literature

Patent Document 1: U.S. Pat. No. 5,282,958
Patent Document 2: Japanese Unexamined Patent Application Publication No. 2006-523136

Non-Patent Literature

Non-Patent Document 1: J. A. Martens et al., *J. Catal.* 239 (2006) 451

SUMMARY OF INVENTION

Technical Problem

However, even the process disclosed in the above-mentioned Patent Document 1 has not provided sufficiently high isomerization selectivity of the catalyst or sufficiently suppressed cracking activity, thus making it difficult to obtain in good yield a desired isoparaffin fraction that is suitable as a lube base oil or fuel base oil from a hydrocarbon oil containing normal paraffin components. Particularly in the production of base oils for high-performance lube oils such as Group III or Group III+ according to the classification of the grades of lube oils prescribed by the American Petroleum Institute, it is necessary to increase the conversion of normal paraffins to a level such that the base oils are substantially free of normal paraffins. In this case, because the cracking reactions of normal paraffins and/or isomerized products, i.e., isoparaffins, actively take place, an intended isoparaffin fraction has not been produced in economical yield.

The catalyst obtained according to the process disclosed in the above-mentioned Patent Document 2 exhibits improved isomerization selectivity; however, the level of isomerization selectivity is not sufficiently high, and further improvement is required.

The present invention has been made in view of the above-described circumstances. An object of the present invention is to provide a hydroisomerization catalyst having sufficiently high isomerization activity and sufficiently suppressed cracking activity that allows a hydrocarbon suitable as a lube base oil and/or a hydrocarbon suitable as a fuel base oil to be produced in good yield from a hydrocarbon feedstock containing normal paraffins; a process for producing the catalyst; a method of dewaxing a hydrocarbon oil using the hydroisomerization catalyst; a process for producing a hydrocarbon; and a process for producing a lube base oil that allows a lube base oil that meets the Group II, Group III, or Group III+ requirements to be economically produced.

Solution to Problem

The present inventors conducted extensive research to solve the above-mentioned object, and consequently found that a catalyst obtained by supporting a specific metal on a support that contains a zeolite obtained by subjecting a zeolite containing an organic template and having a specific structure to ion-exchange treatment, calcining the zeolite at a specific temperature, and modifying the zeolite with a specific metal, and that contains a specific inorganic oxide, has sufficiently high isomerization activity and sufficiently low cracking activity in the hydroprocessing of normal paraffins, i.e., the catalyst has excellent isomerization selectivity. The present inventors also found that an isoparaffin fraction suitable as a high-performance lube base oil having a high viscosity index and low pour point can be produced in high yield by contacting the above-described catalyst with a hydrocarbon feedstock containing waxy components in the presence of hydrogen. The inventors consequently accomplished the present invention based on these findings.

More specifically, the present invention provides a catalyst used for hydroisomerization of a hydrocarbon comprising a support comprising a calcined zeolite modified with at least one metal selected from the group consisting of Na, K, Cs, Mg, Ca, Ba, and K, and having a thermal history that includes heating at 350° C. or more, and at least one inorganic oxide selected from the group consisting of alumina, silica, titania, boria, zirconia, magnesia, ceria, zinc oxide, phosphorus oxide, and a composite oxide containing a combination of at least two or more of these oxides; and at least one metal supported on the support and selected from the group consisting of elements belonging to Groups 8 to 10 of the periodic table, molybdenum and tungsten; wherein the zeolite is prepared from an ion-exchanged zeolite obtained by ion exchange of an organic template-containing zeolite containing an organic template and having a 10-membered ring one-dimensional porous structure in a solution containing ammonium ions and/or protons; and initial heating of the heating at 350° C. or more of the thermal history experienced by the zeolite is conducted within the temperature range from 350 to 450° C.

The periodic table as referred to herein represents the long form of the periodic table designated by the International Union of Pure and Applied Chemistry (IUPAC).

Because the hydroisomerization catalyst of the present invention has the above-described structure, it can function as a catalyst having sufficiently high isomerization activity and sufficiently suppressed cracking activity in the hydroisomerization of normal paraffins. Furthermore, by using the hydroisomerization catalyst of the present invention, even when a hydrocarbon feedstock containing normal paraffins is hythoisomerized in the presence of hydrogen under conditions that sufficiently increase the normal paraffin conversion, it is possible to produce an isoparaffin having a desired number of carbon atoms or more in a remarkably improved yield, as compared to when using conventional catalysts. Thus, the application of the hydroisomerization catalyst of the present invention to catalytic dewaxing of a hydrocarbon feedstock containing normal paraffins allows a hydrocarbon suitable as a lube base oil and/or a hydrocarbon suitable as a fuel base oil to be produced in a sufficiently high yield. With respect to the hydrocarbon suitable as a fuel base oil, particularly hydrocarbons suitable as gas oil base oils can be produced in high yield; and with respect to the hydrocarbon suitable as a lube base oil, particularly hydrocarbons suitable as high-performance lube base oils having high viscosity indices and low pour points, such as Group II, Group III, and Group III+, can be produced in high yield.

In view of achieving a higher level of isomerization selectivity, the zeolite is preferably modified with Cs.

In view of high isomerization selectivity in the hydroisomerization reactions of normal paraffins, the organic template-containing zeolite is preferably at least one selected from the group consisting of a zeolite ZSM-22, a zeolite ZSM-23, and a zeolite ZSM-48.

In view of isomerization selectivity, the inorganic oxide is preferably alumina.

In view of the isomerization selectivity and reaction activity, the metal supported on the support is preferably platinum and/or palladium.

In view of the isomerization selectivity and reaction activity, the molar ratio of silicon atoms to aluminum atoms ([Si]/[Al]) in the organic template-containing zeolite is preferably 10 to 400.

Further, the present invention provides a first process for producing a catalyst used for hydroisomerization of a hydrocarbon, comprising a first step of obtaining an ion-exchanged zeolite by ion exchange of an organic template-containing zeolite containing an organic template and having a 10-membered ring one-dimensional porous structure in a solution containing ammonium ions and/or protons; a second step of obtaining a calcined zeolite by calcining the ion-exchanged zeolite that has not been heated at 350° C. or more by heating within the temperature range from 350 to 450° C.; and a third step of modifying the calcined zeolite with at least one metal selected from the group consisting of Na, K, Cs, Mg, Ca, Ba, and K; the process producing a catalyst comprising a support comprising a calcined zeolite modified with at least one metal selected from the group consisting of Na, K, Cs, Mg, Ca, Ba, and K, and having a thermal history in which initial heating of heating at 350° C. or more is conducted within the temperature range from 350 to 450° C., and at least one inorganic oxide selected from the group consisting of alumina, silica, titania, boria, zirconia, magnesia, ceria, zinc oxide, phosphorus oxide, and a composite oxide containing a combination of at least two or more of these oxides; and at least one metal supported on the support and selected from the group consisting of elements belonging to Groups 8 to 10 of the periodic table, molybdenum and tungsten.

According to the first process for producing a hydroisomerization catalyst of the present invention, by obtaining a catalyst having the above-described structure through the above-described steps, it is possible to achieve a catalyst having excellent isomerization selectivity, in which the isomerization activity is sufficiently high, and the cracking activity is sufficiently suppressed in the hydroisomerization of normal paraffins. Furthermore, the catalyst produced by the above-described process has both excellent isomerization selectivity and isomerization reaction activity, thus allowing a hydrocarbon suitable as a lube base oil and/or a hydrocarbon suitable as a fuel base oil, and, in particular, a hydrocarbon suitable as a high-quality lube base oil, to be stably produced in high yield from a hydrocarbon feedstock containing normal paraffins.

In view of obtaining a catalyst having a higher level of isomerization selectivity, the calcined zeolite is preferably modified with Cs in the third step.

Further, the present invention provides a second process for producing a catalyst used for hydroisomerization of a hydrocarbon, comprising a first step of obtaining an ion-exchanged zeolite by ion exchange of an organic template-containing zeolite containing an organic template and having a 10-membered ring one-dimensional porous structure in a solution containing ammonium ions and/or protons; a second step of obtaining a calcined product by calcining, within the temperature range from 350 to 450° C., a molded product comprising the ion-exchanged zeolite that has not been heated at 350° C. or more, and at least one inorganic oxide selected from the group consisting of alumina, silica, titania, boria, zirconia, magnesia, ceria, zinc oxide, phosphorus oxide, and a composite oxide containing a combination of at least two or more of these oxides; and a third step of modifying the calcined product with at least one metal selected from the group consisting of Na, K, Cs, Mg, Ca, Ba, and K; the process producing a catalyst comprising a support comprising a calcined zeolite modified with at least one metal selected from the group consisting of Na, K, Cs, Mg, Ca, Ba, and K, and having a thermal history in which initial heating of heating at 350° C. or more is conducted within the temperature range from 350 to 450° C., and at least one inorganic oxide selected from the group consisting of alumina, silica, titania, boria, zirconia, magnesia, ceria, zinc oxide, phosphorus oxide, and a composite containing a combination of at least two or more of these oxides; and at least one metal supported on the support and selected from the group consisting of elements belonging to Groups 8 to 10 of the periodic table, molybdenum and tungsten.

According to the second process for producing a hydroisomerization catalyst of the present invention, by obtaining a catalyst having the above-described structure through the above-described steps, it is possible to achieve a catalyst having excellent isomerization selectivity, in which the isomerization activity is sufficiently high, and the cracking activity is sufficiently suppressed in the hydroisomerization of normal paraffins. Furthermore, the catalyst produced by the above-described process has both excellent isomerization selectivity and isomerization reaction activity, thus allowing a hydrocarbon suitable as a lube base oil and/or a hydrocarbon suitable as a fuel base oil, and, in particular, a hydrocarbon suitable as a high-quality lube base oil, to be stably produced in high yield from a hydrocarbon feedstock containing normal paraffins.

In view of obtaining a catalyst having a higher level of isomerization selectivity, the calcined product is preferably modified with Cs in the third step.

Further, the present invention provides a third process for producing a catalyst used for hydroisomerization of a hydrocarbon, comprising a first step of obtaining an ion-exchanged zeolite by ion exchange of an organic template-containing zeolite containing an organic template and having a 10-membered ring one-dimensional porous structure in a solution containing ammonium ions and/or protons; a second step of obtaining a modified zeolite by modifying the ion-exchanged zeolite with at least one metal selected from the group consisting of Na, K, Cs, Mg, Ca, Ba, and K; and a third step of obtaining a modified and calcined zeolite by calcining, within the temperature range from 350 to 450° C., the modified zeolite that has not been heated at 350° C. or more; the process producing a catalyst comprising a support comprising a calcined zeolite modified with at least one metal selected from the group consisting of Na, K, Cs, Mg, Ca, Ba, and K, and having a thermal history in which initial heating of heating at 350° C. or more is conducted within the temperature range from 350 to 450° C., and at least one inorganic oxide selected from the group consisting of alumina, silica, titania, boria, zirconia, magnesia, ceria, zinc oxide, phosphorus oxide, and a composite oxide containing a combination of at least two or more of these oxides; and at least one metal supported on the support and selected from the group consisting of elements belonging to Groups 8 to 10 of the periodic table, molybdenum and tungsten.

According to the third process for producing a hydroisomerization catalyst of the present invention, by obtaining a catalyst having the above-described structure through the above-described steps, it is possible to achieve a catalyst having excellent isomerization selectivity, in which the isomerization activity is sufficiently high, and the cracking activity is sufficiently suppressed in the hydroisomerization of normal paraffins. Furthermore, the catalyst produced by the above-described process has both excellent isomerization selectivity and isomerization reaction activity, thus allowing a hydrocarbon suitable as a lube base oil and/or a hydrocarbon suitable as a fuel base oil, and, in particular, a hydrocarbon suitable as a high-quality lube base oil, to be stably produced in high yield from a hydrocarbon feedstock containing normal paraffins.

In view of obtaining a catalyst having a higher level of isomerization selectivity, the ion-exchanged zeolite is preferably modified with Cs in the second step.

In each of the above-described first, second, and third processes for producing a hydroisomerization catalyst of the present invention, in view of obtaining a catalyst having high isomerization selectivity in the hydroisomerization reaction of normal paraffins, the organic template-containing zeolite is preferably at least one selected from the group consisting of a zeolite ZSM-22, a zeolite ZSM-23, and a zeolite ZSM-48.

Moreover, in view of obtaining a catalyst having excellent isomerization selectivity, the inorganic oxide is preferably alumina.

Furthermore, in view of obtaining a catalyst having excellent isomerization selectivity and reaction activity, the metal supported on the support is preferably platinum and/or palladium.

Moreover, in view of obtaining a catalyst having excellent isomerization selectivity and reaction activity, the molar ratio of silicon atoms to aluminum atoms ([Si]/[Al]) in the organic template-containing zeolite is preferably 10 to 400.

Further, the present invention provides a method of dewaxing a hydrocarbon oil comprising contacting, in the presence of hydrogen, a hydrocarbon oil containing normal paraffins having 10 or more carbon atoms, with the above-described hydroisomerization catalyst of the present invention, or a hydroisomerization catalyst obtained by the first, second, or third process of the present invention, thereby converting a portion or all of the normal paraffins to isoparaffins.

In the method of dewaxing a hydrocarbon oil of the present invention, at least one selected from the group consisting of hydrocracked vacuum gas oils, hydrocracked atmospheric residual oils, hydrocracked vacuum residual oils, hydrodesulfurized vacuum gas oils, hydrodesulfurized atmospheric residual oils, hydrodesulfurized vacuum residual oils, slack waxes, dewaxed oils, paraffinic waxes, microcrystalline waxes, petrolatum, and Fischer-Tropsch synthesis waxes can be fed as the hydrocarbon oil.

Further, the present invention provides a process for producing a hydrocarbon comprising contacting, in the presence of hydrogen, a hydrocarbon feedstock containing normal paraffins having 10 or more carbon atoms, with the hydroisomerization catalyst of the present invention, or a hydroisomerization catalyst obtained by the first, second, or third process of the present invention.

In the process for producing a hydrocarbon of the present invention, at least one member selected from the group consisting of hydrocracked vacuum gas oils, hydrocracked atmospheric residual oils, hydrocracked vacuum residual oils, hydrodesulfurized vacuum gas oils, hydrodesulfurized atmospheric residual oils, hydrodesulfurized vacuum residual oils, slack waxes, dewaxed oils, paraffinic waxes, microcrystalline waxes, petrolatum, and Fischer-Tropsch synthesis waxes can be fed as the hydrocarbon feedstock.

Further, the present invention provides a process for producing a lube base oil comprising contacting, in the presence of hydrogen, a hydrocarbon feedstock containing normal paraffins having 10 or more carbon atoms, with the hydroisomerization catalyst of the present invention, or a hydroisomerization catalyst obtained by the first, second, or third process of the present invention, under conditions that give substantially 100 mass % conversion of the normal paraffins, as defined by the following expression (I):

$$\text{Normal paraffin conversion (\%)} = \left[1 - \left(\frac{\text{Total mass of the normal paraffins having } Cn \text{ or more contained in the hydrocarbon oil after contacting}}{\text{Total mass of the normal paraffins having } Cn \text{ or more contained in the hydrocarbon oil before contacting}}\right)\right] \times 100 \quad (1)$$

wherein $Cn$ represents a minimum number of carbon atoms of the normal paraffins having 10 or more carbon atoms contained in the hydrocarbon feedstock before contacting.

According to the process for producing a lube base oil of the present invention, a hydrocarbon suitable as a lube base oil can be produced in high yield by hydroprocessing a hydrocarbon feedstock under the above-described conditions using the hydroisomerization catalyst of the present invention, thereby allowing a lube base oil that meets the Group II, Group III, or Group III+ requirements to be economically produced.

In the process for producing a lube base oil of the present invention, the hydrocarbon feedstock after being contacted with the hydroisomerization catalyst is preferably further hydrofinished, and then distilled under vacuum.

Advantageous Effects of Invention

The present invention can provide a hydroisomerization catalyst having sufficiently high isomerization activity and sufficiently suppressed cracking activity that allows a hydrocarbon suitable as a lube base oil and/or a hydrocarbon suitable as a fuel base oil to be produced in high yield from a hydrocarbon feedstock containing normal paraffins; a process for producing the catalyst; a method of dewaxing a hydrocarbon oil using the hydroisomerization catalyst; a process for producing a hydrocarbon; and a process for producing a lube base oil that allows a lube base oil that meets the Group II, Group III, or Group III+ requirements to be economically produced.

BRIEF DESCRIPTION OF THE DRAWINGS

FIG. 1 is a graph showing the distribution of the numbers of carbon atoms in wax feedstock.

DESCRIPTION OF EMBODIMENTS

The hydroisomerization catalyst of the present invention is produced according to a specific process and is thereby provided with its features. The hydroisomerization catalyst comprises a support comprising a calcined zeolite modified with at least one metal selected from the group consisting of Na, K, Cs, Mg, Ca, Ba, and K, and having a thermal history that includes heating at 350° C. or more, and at least one inorganic oxide selected from the group consisting of alumina, silica, titania, boria, zirconia, magnesia, ceria, zinc oxide, phosphorus oxide, and a composite oxide containing a combination of at least two or more of these oxides; and at least one metal supported on the support and selected from the group consisting of elements belonging to Groups 8 to 10 of the periodic table, molybdenum and tungsten; wherein the zeolite is prepared from an ion-exchanged zeolite obtained by ion exchange of an organic template-containing zeolite containing an organic template and having a 10-membered ring one-dimensional porous structure in a solution containing ammonium ions and/or protons; and initial heating of the heating at 350° C. or more of the thermal history experienced by the zeolite is conducted within the temperature range from 350 to 450° C.

Examples of processes for producing the above-described catalyst include the following first to third processes.

The first process is a process for producing the above-described catalyst, which comprises a first step of obtaining an ion-exchanged zeolite by ion exchange of an organic template-containing zeolite containing an organic template and having a 10-membered ring one-dimensional porous structure in a solution containing ammonium ions and/or protons; a second step of obtaining a calcined zeolite by calcining the ion-exchanged zeolite that has not been heated at 350° C. or more by heating within the temperature range from 350 to 450° C.; and a third step of modifying the calcined zeolite with at least one metal selected from the group consisting of Na, K, Cs, Mg, Ca, Ba, and K.

The second process is a process for producing the above-described catalyst, which comprises a first step of obtaining an ion-exchanged zeolite by ion exchange of an organic template-containing zeolite containing an organic template and having a 10-membered ring one-dimensional porous structure in a solution containing ammonium ions and/or protons; a second step of obtaining a calcined product by calcining, within the temperature range from 350 to 450° C., a molded product comprising the ion-exchanged zeolite that has not been heated at 350° C. or more, and at least one inorganic oxide selected from the group consisting of alumina, silica, titania, boria, zirconia, magnesia, ceria, zinc oxide, phosphorus oxide, and a composite oxide containing a combination of at least two or more of these oxides; and a third step of modifying the calcined product with at least one metal selected from the group consisting of Na, K, Cs, Mg, Ca, Ba, and K.

The third process is a process for producing the above-described catalyst, which comprises a first step of obtaining an ion-exchanged zeolite by ion exchange of an organic template-containing zeolite containing an organic template and having a 10-membered ring one-dimensional porous structure in a solution containing ammonium ions and/or protons; a second step of obtaining a modified zeolite by modifying the ion-exchanged zeolite with at least one metal selected from the group consisting of Na, K, Cs, Mg, Ca, Ba, and K; and a third step of obtaining a modified and calcined zeolite by calcining, within the temperature range from 350 to 450° C., the modified zeolite that has not been heated at 350° C. or more.

The hydroisomerization catalyst of the present invention will be described below in accordance with an embodiment of the above-described second process.

The organic template-containing zeolite, which is used as a starting material of a calcined zeolite (a) modified with at least one metal selected from the group consisting of Na, K, Cs, Mg, Ca, Ba, and K, and having a thermal history in which initial heating of heating at 350° C. or more is conducted within the temperature range from 350 to 450° C., which constitutes the hydroisomerization catalyst of the present invention, preferably has a one-dimensional porous structure made of a 10-membered ring, in view of achieving a high level of both high isomerization activity and suppressed cracking activity in the hydroisomerization reactions of normal paraffins. Examples of such zeolites include AEL, EUO, FER, HEU, MEL, MFI, NES, TON, MTT, WEI, and ZSM-48. It is noted that the above three alphabet letters designate framework-type codes assigned to various structures of classified molecular sieve-type zeolites by the Structure Commision of the International Zeolite Association. It is also noted that zeolites having the same topology are collectively designated by the same code.

Among the above-mentioned zeolites having 10-membered ring one-dimensional porous structures, preferred as the organic template-containing zeolite are zeolites having the TON and MTT structures, and zeolite ZSM-48, in view of high isomerization activity and low cracking activity. Zeolite ZSM-22 is more preferred among zeolites having the TON structure, and zeolite ZSM-23 is more preferred among zeolites having the MTT structure.

The organic template-containing zeolite containing an organic template and having a 10-membered ring one-dimensional porous structure, which is used as a starting material of the zeolite (a) that constitutes the hydroisomerization catalyst of the present invention, is hydrothermally synthesized according to a known method using a silica source, an alumina source, and an organic template that is added to construct the predetermined porous structure described above.

The organic template is an organic compound having an amino group, ammonium group, or the like, and is selected according to the structure of the zeolite to be synthesized; however, the organic template is preferably an amine derivative. Specifically, the organic template is preferably at least one selected from the group consisting of alkylamines, alkyldiamines, alkyltriamines, alkyltetramines, pyrrolidine, piperazine, aminopiperazine, alkylpentamines, alkylhexamines, and their derivatives.

The molar ratio of the silicon element to aluminum element ([Si]/[Al]; hereinafter referred to as the "Si/Al ratio") that constitute the organic template-containing zeolite having a 10-membered ring one-dimensional porous structure is preferably 10 to 400, and more preferably 20 to 350. If the Si/Al ratio is less than 10, although the activity for the conversion of normal paraffins increases, the isomerization selectivity to isoparaffins tends to decrease, and cracking reactions tend to sharply increase as the reaction temperature increases, which is undesirable. Conversely, if the Si/Al ratio is more than 400, catalytic activity needed for the conversion of normal paraffins cannot be easily obtained, which is undesirable.

The synthesized organic template-containing zeolite, which has preferably been washed and dried, typically has alkali metal cations as counter cations, and incorporates the organic template in its porous structure. The zeolite containing an organic template, which is used for producing the hydroisomerization catalyst of the present invention, is preferably in such a synthesized state, i.e., preferably, the zeolite has not been subjected to calcination treatment for removing the organic template incorporated therein.

The organic template-containing zeolite is subsequently ion-exchanged in a solution containing ammonium ions and/or protons. By the ion-exchange treatment, the counter cations contained in the organic template-containing zeolite are exchanged into ammonium ions and/or protons. At the same time, a portion of the organic template incorporated in the organic template-containing zeolite is removed.

The solution used for the ion-exchange treatment is preferably a solution that uses a solvent containing at least 50 vol % of water, and more preferably an aqueous solution. Examples of compounds for supplying ammonium ions into the solution include various inorganic and organic ammonium salts, such as ammonium chloride, ammonium sulfate, ammonium nitrate, ammonium phosphate, and ammonium acetate. On the other hand, mineral acids such as hydrochloric acid, sulfuric acid, and nitric acid are typically used as compounds for supplying protons into the solution. The ion-exchanged zeolite (herein, an ammonium-form zeolite) obtained by ion exchange of the organic template-containing zeolite in the presence of ammonium ions releases ammonia during subsequent calcination, and the counter cations are converted into protons to form Bronsted acid sites. Ammonium ions are preferred as the cationic species used for the ion exchange. The amount of ammonium ions and/or protons contained in the solution is preferably adjusted to 10 to 1000 equivalents relative to the total amount of the counter cations and organic template contained in the organic template-containing zeolite used.

The ion-exchange treatment may be applied to the organic template-containing zeolite alone in powder form; alternatively, prior to the ion-exchange treatment, the organic template-containing zeolite may be mixed with an inorganic oxide, which is a binder, and molded, and the ion-exchange treatment may be applied to the resulting molded product. However, if the molded product in its uncalcined state is subjected to the ion-exchanged treatment, the problem of collapsing and powdering of the molded product will easily arise; therefore, it is preferred to subject the organic template-containing zeolite in powder form to the ion-exchange treatment.

The ion-exchange treatment is preferably performed according to a standard method, i.e., a method in which the organic template-containing zeolite is immersed in a solution, preferably an aqueous solution, containing ammonium ions and/or protons, and the solution is stirred and fluidized. The stirring or fluidization is preferably performed under heating to improve the ion-exchange efficiency. In the present invention, it is particularly preferred to use a method in which the aqueous solution is heated, boiled, and ion-exchanged under reflux.

Further, in view of improving the ion-exchange efficiency, during the ion exchange of the zeolite in a solution, the solution is preferably exchanged with a fresh one once or twice or more, and more preferably exchanged with a fresh one once or twice. When the solution is exchanged once, the ion-exchange efficiency can be improved by, for example, immersing the organic template-containing zeolite in a solution containing ammonium ions and/or protons, and heating the solution under reflux for 1 to 6 hours, followed by exchanging the solution with a fresh one, and further heating under reflux for 6 to 12 hours.

By the ion-exchange treatment, substantially all of the counter cations such as an alkali metal in the zeolite can be exchanged into ammonium ions and/or protons. On the other hand, with respect to the organic template incorporated in the zeolite, although a portion of the organic template is removed by the ion-exchange treatment, it is generally difficult to remove all of the organic template even if the ion-exchange treatment is repeatedly performed, resulting in a portion of the organic template remaining inside the zeolite.

Next, it is preferred to mix the ion-exchanged zeolite obtained by the above-described method with an inorganic oxide, which is a binder, and mold the resulting composition to form a molded product. The purpose of mixing the ion-exchanged zeolite with an inorganic oxide is to increase the mechanical strength of the support (in particular, a particulate support) obtained by calcining the molded product to a degree that can withstand practical applications; however, the present inventors have found that the selection of the type of inorganic oxide affects the isomerization selectivity of the hydroisomerization catalyst. From this viewpoint, at least one inorganic oxide selected from alumina, silica, titania, boria, zirconia, magnesia, ceria, zinc oxide, phosphorus oxide, and a composite oxide containing a combination of at least two or more of these oxides can be used as the inorganic oxide. Among the above, alumina is preferred in view of further improving the isomerization selectivity of the hydroisomerization catalyst. The phrase "composite oxide containing a combination of at least two or more of these oxides" is a composite oxide containing at least two components from alumina, silica, titania, boria, zirconia, magnesia, ceria, zinc oxide, and phosphorus oxide, but is preferably an alumina-based composite oxide containing 50 mass % or more of an alumina component based on the composite oxide.

The proportion of the ion-exchanged zeolite to the inorganic oxide in the above-mentioned composition is preferably 10:90 to 90:10, and more preferably 30:70 to 85:15, in terms of the mass ratio of the ion-exchanged zeolite to the inorganic oxide. If this ratio is less than 10:90, the activity of the hydroisomerization catalyst tends to be insufficient, which is undesirable. Conversely, if the ratio is more than 90:10, the mechanical strength of the support obtained by molding and calcining the composition tends to be insufficient, which is undesirable.

Although the method for mixing the ion-exchanged zeolite with the inorganic oxide is not particularly limited, a general method can be employed, such as, for example, a method in which a suitable amount of a liquid such as water is added to the powders of both components to form a viscous fluid, and the fluid is kneaded in a kneader or the like.

The composition containing the ion-exchanged zeolite and inorganic oxide, or a viscous fluid containing the composition, is molded by extrusion or other methods, and is preferably dried, to form a particulate molded product. Although the shape of the molded product is not particularly limited, the molded product may, for example, have a cylindrical shape, pellet shape, spherical shape, or irregular tubular shape having a three leaf-shaped or four leaf-shaped cross section. Although the size of the molded product is not particularly limited, the molded product is preferably, for example, about 1 to 30 mm in long axis, and about 1 to 20 mm in short axis, in view of the ease of handling, the load density in the reactor, etc.

Next, the thus-obtained molded product is preferably calcined in an atmosphere containing molecular oxygen, and more preferably in an air atmosphere, at a temperature of 350 to 450° C., preferably 350 to 430° C., and more preferably 350 to 420° C., to give a calcined support having a thermal history that includes heating at 350° C. or more. The phrase "in an atmosphere containing molecular oxygen" means contacting the molded product with gases containing oxygen gas, and, particularly preferably with air. The calcination time is not particularly limited, but is preferably 1 to 24 hours.

By the calcination described above, the ion-exchanged zeolite that constitutes the molded product turns into a calcined zeolite, and the inorganic oxide turns into a calcined inorganic oxide.

In this embodiment, if the calcination temperature is lower than 350° C., the removal of the organic template tends not to proceed sufficiently, or the removal tends to require a long time, and further, the mechanical strength of the support tends not to be improved sufficiently, which is undesirable. Conversely, if the calcination temperature is higher than 450° C., the isomerization selectivity of the resulting hydroisomerization catalyst tends not to be improved sufficiently, which is undesirable. It is extremely important to calcine the ion-exchanged zeolite that has not been heated at 350° C. or more and containing residual organic template at a relatively low temperature as defined above, in order to improve the isomerization selectivity of the hydroisomerization catalyst of the present invention.

As described above, the ion-exchanged zeolite alone in powder form may be calcined as an alternative to calcining the molded product obtained by molding the composition prepared by mixing the ion-exchanged zeolite with the inorganic oxide. In this case, however, it is necessary to calcine a molded product obtained by molding a composition prepared by mixing the resulting calcined zeolite with an inorganic oxide at a temperature of 350° C. or more, for example, at a temperature within the range from 350 to 450° C. and/or within the temperature of more than 450° C. and 650° C. or less, for the purpose of imparting mechanical strength to the molded product.

The support may be calcined by heating within the temperature range from 350 to 450° C., and by further heating within the temperature range of more than 450° C. and 650° C. or less, preferably in an atmosphere containing molecular oxygen, and more preferably in an air atmosphere. The calcination by further heating at more than 450° C. and 650° C. or less, in addition to heating at 350 to 450° C., allows the mechanical strength of the support to be further improved, without significantly affecting the hydroisomerization selectivity of the resulting catalyst. Therefore, when catalyst particles having a higher mechanical strength are desired, it is preferred to perform calcination by the two-stage heating described above. If the heating temperature in the subsequent stage is 450° C. or less, it tends to be difficult to further improve the mechanical strength of the support. Conversely, if the heating temperature in the subsequent stage is more than 650° C., the environment of the aluminum atoms that involve the formation of active sites on the zeolite tends to change, resulting in increased cracking activity, which is undesirable. Further, in view of maintaining the isomerization selectivity, the heating temperature in the subsequent stage is more preferably a temperature within the range of more than 450° C. and 600° C. or less.

In this embodiment, at least one metal selected from the group consisting of Na, K, Cs, Mg, Ca, Ba, and K is added to the thus-obtained calcined product (the support) having a thermal history that includes heating at 350° C. or more, thereby modifying the zeolite contained in the calcined product. The present inventors believe that these metals reduce the number of strong acid sites on the catalyst, thereby lowering the selectivity for cracking versus isomerization, leading to improved isomerization selectivity of the catalyst. The addition of these metals can be performed by impregnation, ion exchange, and other methods. Specifically, for example, a solution containing a cationic salt of any of the above-mentioned metals may be contacted with the calcined product. Examples of such salts include hydroxides, chlorides, and other halides; nitrates; and sulfates.

The amount of the zeolite modification with any of the above-mentioned metals is preferably such that the molar amount of the metal atoms in the zeolite is 0.001 to 0.5 times the molar amount of aluminum atoms in the zeolite.

In view of achieving a higher level of isomerization selectivity, the zeolite is preferably modified with Cs. The present inventors assume that the reason for the improved isomerization selectivity of the catalyst is as follows. It is believed that, because Cs ions are greater in pore size than the zeolite, they cannot enter into the pores, and can thereby block only strong acid sites on the outer surface of the catalyst. This allows strong acid sites near the pores, which are believed to be isomerization active sites, to remain without being blocked, thereby sufficiently ensuring the isomerization reaction activity while suppressing the cracking reactions.

When the zeolite is modified with Cs, the amount of the modification is preferably such that the molar amount of cesium atoms in the zeolite is 0.001 to 0.05 times the molar amount of aluminum atoms in the zeolite.

In this embodiment, the support, i.e., the calcined extrudate or molded particles, is metal-modified by the addition of any of the above-mentioned metals; however, as shown in the first or third process described above, the ion-exchanged, uncalcined particles (the ion-exchanged zeolite) or the calcined particles (the calcined zeolite that has been calcined by heating the ion-exchanged zeolite within the range from 350 to 450° C.) may be metal-modified.

Next, in this embodiment, it is preferred that at least one metal (hereinafter sometimes referred to as an "active metal") selected from the group consisting of metals belonging to Groups 8 to 10 of the periodic table, molybdenum and tungsten be supported on the support containing a zeolite that has a thermal history that includes heating at 350° C. or more, is calcined, and is modified with at least one metal selected from the group consisting of Na, K, Cs, Mg, Ca, Ba, and K, and containing a calcined inorganic oxide.

Examples of metals belonging to Groups 8 to 10 of the periodic table include iron, ruthenium, osmium, cobalt, rhodium, iridium, nickel, palladium, and platinum. Among these metals, platinum and/or palladium is preferred, and platinum is particularly preferred, in view of the activity, isomerization selectivity, and durability of activity. The above-mentioned active metals can be used alone or in a combination of two or more. Moreover, when the hydroisomerization catalyst of the present invention is used for hydroisomerization of a hydrocarbon oil containing many ion-containing compounds and/or nitrogen-containing compounds, it is preferred that the hydroisomerization catalyst contain, as active metals, a combination such as nickel-cobalt, nickel-molybdenum, cobalt-molybdenum, nickel-molybdenum-cobalt, or nickel-tungsten-cobalt, in view of the durability of catalytic activity.

The method for supporting the above-mentioned active metal on the support is not particularly limited; known methods are employed, such as impregnation methods (equilibrium adsorption, pore filling, and incipient wetting) using compounds containing the above-mentioned active metal elements (hereinafter sometimes referred to as "active metal precursors"), ion-exchange methods, and the like.

Examples of active metal precursors include hydrochlorides, sulfates, nitrates, and complex compounds of the above-mentioned active metals. When the active metal is platinum, active metal precursors that are preferably used include chloroplatinic acid, tetraamminedinitroplatinum, dinitroaminoplatinum, and tetraamminedichloroplatinum.

The total amount of the active metal supported on the support containing the zeolite (a) of the present invention and the calcined inorganic oxide is preferably 0.001 to 20 mass %, based on the mass of the support. If the total amount of the supported metal is less than 0.001 mass %, it will be difficult to impart a predetermined hydrogenation/dehydrogenation function to the catalyst. Conversely, if the amount of the supported metal is more than 20 mass %, conversion of hydrocarbons into lighter products on the active metal by cracking tends to easily proceed, causing the yield of a desired fraction to decrease, and further causing the catalyst costs to increase, which is undesirable.

The active metal may be supported on either one or both of the zeolite (a) of the present invention that constitutes the support and the calcined inorganic oxide. When the hydroisomerization catalyst of the present invention is produced by a method in which an active metal is supported on the support by, for example, an impregnation method, the distribution of sites on which the active metal is supported is mainly determined by the affinity between the active metal precursor used in the supporting, and the zeolite (a) and calcined inorganic oxide.

The supporting of an active metal is not limited to an embodiment in which the active metal is supported on the molded and calcined support. For example, an active metal may be supported on the ion-exchanged zeolite in powder form, or on the calcined zeolite obtained by calcining the ion-exchanged zeolite at a temperature of 350 to 450° C., or may be supported on the inorganic oxide in power form; alternatively, an active metal may be supported on both of the zeolite and inorganic oxide.

It is preferred that the support on which the active metal component is supported be calcined preferably in an atmosphere containing molecular oxygen, mainly for the purpose of removing the anionic component or ligand component contained in the active metal precursor. The calcination temperature is preferably 250 to 600° C., and more preferably 300 to 500° C. The atmosphere containing molecular oxygen is preferably air. The calcination time is typically about 0.5 to 20 hours. By calcination treatment as described above, the active metal precursor is converted into an elemental metal, its oxide, or a similar species.

It is preferred that, subsequent to the calcination treatment, the hydroisomerization catalyst of the present invention be subjected to reduction treatment, preferably after the catalyst is loaded in the reactor for conducting the hydroisomerization reaction. Specifically, the reduction treatment is preferably performed for about 0.5 to 5 hours in an atmosphere containing molecular hydrogen, and preferably under a stream of hydrogen gas, preferably at 250 to 500° C., and more preferably at 300 to 400° C. This step further ensures that high activity for dewaxing a hydrocarbon oil can be imparted to the catalyst.

In the hydroisomerization catalyst of the present invention, a metal other than the metals belonging to Groups 8 to 10 of the periodic table, molybdenum, and tungsten may further be supported on the zeolite (a) and/or calcined inorganic oxide, within a range such that the effects of the present invention are not impaired.

<Method of Dewaxing a Hydrocarbon Oil>

Next, the method of dewaxing a hydrocarbon oil is described. The method of dewaxing a hydrocarbon oil of the present invention comprises the step of contacting, in the presence of hydrogen, a hydrocarbon oil containing normal paraffins having 10 or more carbon atoms, with the above-described hydroisomerization catalyst of the present invention, thereby converting a portion or all of the normal paraffins to isoparaffins.

The hydrocarbon oil (the oil to be treated) that is subjected to the method of dewaxing a hydrocarbon oil of the present invention is not particularly limited as long as it contains normal paraffins having 10 or more carbon atoms; preferably, the hydrocarbon oil contains normal paraffins having 15 or more carbon atoms. Specific examples of hydrocarbon oils include various hydrocarbon oils ranging from relatively light distillate fractions such as kerosenes and jet fuels, to high boiling feedstocks such as whole crude petroleum, reduced crudes, vacuum tower residual oils, vacuum residual oils, cycle oils, synthetic crudes (e.g., shale oils, tar oils, etc.), gas oils, vacuum gas oils, foot's oils, fuel fractions or waxy components derived from FT synthesis oils, and other heavy oils. These hydrocarbon oils may also contain, in addition to normal paraffins, waxy components composed of naphthenic hydrocarbons having long straight-chain alkyl groups on side chains, or aromatic hydrocarbons.

Particularly preferred as hydrocarbon oils to be dewaxed by the method of dewaxing a hydrocarbon oil of the present invention are hydrocarbon oils composed of hydrocarbons having boiling points of about 180° C. or more, and having 10 or more carbon atoms. Hydrocarbon oils lighter than these hydrocarbon oils typically contain substantially no waxy components that affect the low-temperature fluidity; therefore, the need to dewax these hydrocarbon oils is low, and hence, the effects of the present invention are unlikely achieved.

Conversely, it is particularly effective to apply the dewaxing method of the present invention to distillate feedstocks containing waxy components such as middle distillate feedstocks including gas oils, kerosenes, and jet fuels, lube oil feedstocks, heating oils, and other distillate fractions whose pour point and viscosity need to be maintained within a predetermined range. Examples of such hydrocarbon oils include hydroprocessed or hydrocracked gas oils, heavy gas oils, vacuum gas oils, atmospheric residual oils, vacuum residual oils, lube oil raffinates, lube oil feedstocks, brightstocks, slack waxes (crude waxes), foot's oils, deoiled waxes, paraffinic waxes, microcrystalline waxes, petrolatum, synthetic oils, FT synthesis oils, high-pour-point polyolefins, and straight-chain α-olefin waxes. These hydrocarbon oils can be used alone or in a combination of two or more.

In particular, the hydrocarbon oil is preferably at least one selected from the group consisting of hydrocracked vacuum gas oils, hydrocracked atmospheric residual oils, hydrocracked vacuum residual oils, hydrodesulfurized vacuum gas oils, hydrodesulfurized atmospheric residual oils, hydrodesulfurized vacuum residual oils, slack waxes, dewaxed oils, paraffinic waxes, microcrystalline waxes, petrolatum, and Fischer-Tropsch synthesis waxes.

In the method of dewaxing a hydrocarbon oil of the present invention, examples of reaction conditions under which at least a portion of the normal paraffins is converted to isoparaffins include the following conditions.

The temperature of the hydroisomerization reaction is preferably 200 to 450° C., and more preferably 220 to 400° C. If the reaction temperature is below 200° C., the isomerization of the normal paraffins contained in the hydrocarbon oil as a feedstock tends not to easily proceed, resulting in insufficient reduction and removal of the waxy components. Conversely, if the reaction temperature is more than 450° C., cracking of the hydrocarbon oil tends to be significant, resulting in a reduced yield of a desired hydrocarbon.

The pressure in the hydroisomerization reaction is preferably 0.1 to 20 MPa, and more preferably 0.5 to 15 MPa. If the reaction pressure is below 0.1 MPa, catalyst deterioration due to the formation of coke tends to be accelerated. Conversely, if the reaction pressure is more than 20 MPa, construction costs for the apparatus tend to increase, making it difficult to realize an economic process.

The liquid hourly space velocity of the hydrocarbon oil relative to the catalyst is preferably 0.01 to 100 $hr^{-1}$, and more preferably 0.1 to 50 $hr^{-1}$. If the liquid hourly space velocity is less than 0.01 $hr^{-1}$, excessive cracking of the hydrocarbon oil tends to easily proceed, resulting in lowered production efficiency for a desired hydrocarbon. Conversely, if the liquid hourly space velocity is more than 100 $hr^{-1}$, the isomerization of the normal paraffins contained in the hydrocarbon oil tends not to easily proceed, resulting in insufficient reduction and removal of the waxy components.

The feed ratio of hydrogen to hydrocarbon oil is preferably 100 to 1000 $Nm^3/m^3$, and more preferably 200 to 800 $Nm^3/m^3$. If the feed ratio is less than 100 $Nm^3/m^3$, for example, when the feedstock contains sulfur and nitrogen compounds, hydrogen sulfide and ammonia gas produced by desulfurization and denitrification reactions that accompany the isomerization reaction tend to adsorb onto and poison the active metal on the catalyst, thus making it difficult to achieve predetermined catalytic performance. Conversely, if the feed ratio is more than 1000 Nm$^3$/m$^3$, hydrogen feed equipment having increased capacity tends to be required, making it difficult to realize an economical process.

The conversion of normal paraffins in the hydroisomerization reaction in the method of dewaxing a hydrocarbon oil of the present invention is adjusted as desired according to the use of the resulting hydrocarbon.

<Process for Producing a Hydrocarbon>

The process for producing a hydrocarbon of the present invention comprises the step of contacting, in the presence of hydrogen, a hydrocarbon feedstock containing normal paraffins having 10 or more carbon atoms, with the hydroisomerization catalyst of the present invention. The hydrocarbon oils mentioned above are usable as the hydrocarbon feedstock that is subjected to the process for producing a hydrocarbon of the present invention. The above-described reaction conditions used in the method of dewaxing a hydrocarbon oil are preferable as the reaction conditions used in the above step.

<Process for Producing a Lube Base Oil>

Next, the process for producing a lube base oil of the present invention is described. The process for producing a lube base oil of the present invention comprises contacting, in the presence of hydrogen, a hydrocarbon feedstock containing normal paraffins having 10 or more carbon atoms, with the above-described hydroisomerization catalyst of the present invention, under conditions that give substantially 100 mass % conversion of the normal paraffins, as defined by the following expression (I):

$$\text{Normal paraffin conversion (\%)} = \left[ 1 - \frac{\left( \begin{array}{c} \text{Total mass of the normal paraffins} \\ \text{having } Cn \text{ or more contained} \\ \text{in the hydrocarbon oil after contacting} \end{array} \right)}{\left( \begin{array}{c} \text{Total mass of the normal paraffins} \\ \text{having } Cn \text{ or more contained} \\ \text{in the hydrocarbon oil before contacting} \end{array} \right)} \right] \times 100 \quad (1)$$

wherein Cn represents a minimum number of carbon atoms of the normal paraffins having 10 or more carbon atoms contained in the hydrocarbon feedstock before contacting.

The phrase "substantially 100 mass % conversion" means that the amount of normal paraffins contained in the hydrocarbon oil after contacting is 0.1 mass % or less.

The hydrocarbon feedstock that is subjected to the process for producing a lube base oil of the present invention is not particularly limited as long as it contains normal paraffins having 10 or more carbon atoms; however, the hydrocarbon feedstock preferably contains a hydrocarbon oil having an initial boiling point higher than that of a desired lube base oil. Examples suitable as such feedstocks include petroleum fractions, synthetic oils and waxes, and the like that are fractions having boiling points of more than 360° C. as calculated at atmospheric pressure; specific examples include heavy gas oils, vacuum gas oils, atmospheric residual oils, vacuum residual oils, lube oil raffinates, brightstocks, slack waxes (crude waxes), foot's oils, deoiled waxes, paraffinic waxes, microcrystalline waxes, petrolatum, synthetic oils, FT synthesis oils, high-pour-point polyolefins, and straight-chain α-olefin waxes. These hydrocarbon feedstocks can be used alone or in a combination of two or more. Further, these oils have preferably been hydroprocessed or lightly hydrocracked. These treatments can reduce or remove sulfur-containing compounds, nitrogen-containing compounds, and other substances that cause the activity of the hydroisomerization catalyst to decrease, and aromatic hydrocarbons, naphthenic hydrocarbons, and other substances that cause the viscosity index of the lube base oil to decrease.

By contacting any of the above-mentioned relatively heavy hydrocarbon oils as a feedstock with the hydroisomerization catalyst of the present invention in the presence of hydrogen, it is possible to allow the isomerization of the normal paraffins contained in the hydrocarbon oil, i.e., the dewaxing reaction of the hydrocarbon oil, to proceed, while sufficiently suppressing the conversion of the hydrocarbon oil into lighter products. In this way, hydrocarbons containing 90 vol % or more of fractions having boiling points of more than 360° C. as calculated at atmospheric pressure can be produced in high yield. Moreover, according to the process for producing a lube base oil of the present invention, a base oil containing many branched-chain isomers can be produced. In particular, for a high-quality lube base oil, it is required that the amount of normal paraffins be 0.1 mass % or less; according to the process for producing a base oil of the present invention, a lube base oil that meets this level of requirement can be produced in high yield.

In the hydroisomerization of a hydrocarbon feedstock containing normal paraffins, it is possible to reduce the amount of normal paraffins contained in the resulting reaction product, by, for example, increasing the reaction temperature to thereby improve the normal paraffin conversion, resulting in improved low-temperature fluidity of the hydrocarbon oil. However, increasing the reaction temperature promotes the cracking reactions of the hydrocarbon oil as a feedstock and isomerized products, thereby increasing the amount of light fractions together with improving the normal paraffin conversion. Such an increase in light fractions is responsible for reducing the viscosity index of the hydrocarbon oil; therefore, in order to maintain the performance of a lube base oil within a predetermined range, it is necessary to separate and remove these light fractions by, for example, distillation. Particularly in the production of high-performance lube base oils such as Group II, Group III, or Group III+ according to the classification of the grades of lube oils prescribed by the American Petroleum Institute by catalytic dewaxing of the hydrocarbon feedstock, it is necessary to increase the normal paraffin conversion in the hydrocarbon oil as a feedstock up to substantially 100%. With conventional processes for producing lube base oils using catalysts for catalytic dewaxing, the yields of the above-mentioned high-performance lube base oils are extremely low under conditions that give substantially 100% normal paraffin conversion. As opposed to this, according to the process for producing a lube base oil of the present invention, it is possible to maintain the yields of the above-mentioned high-performance lube base oils at high levels, even when the hydroprocessing step is performed under conditions that give substantially 100% normal paraffin conversion.

The equipment for carrying out the method of dewaxing a hydrocarbon oil, the process for producing a hydrocarbon, and the process for producing a lube base oil of the present invention is not particularly limited, and known equipment can be employed. The reaction equipment may be any of a continuous flow-type, a batch-type, and a semi-batch-type; however, a continuous flow-type is preferred in view of productivity and efficiency. The catalyst bed may be any of a fixed bed, a fluidized bed, and a stirred bed; however, a fixed bed is preferred in view of equipment costs and the like. The reaction phase is preferably a mixed phase of gas and liquid.

In the method of dewaxing a hydrocarbon oil, the process for producing a hydrocarbon, and the process for producing a lube base oil of the present invention, the hydrocarbon oil as a feedstock to be fed may be hydroprocessed or hydrocracked as a stage prior to the dewaxing step utilizing the hydroisomerization reaction described above. Known equipment, catalysts, and reaction conditions can be used for the hydroprocessing or hydrocracking. By carrying out these pre-treatments, it is possible to maintain the activity of the hydroisomerization catalyst of the present invention over an extended period of time, and to reduce the amount of substances of concern such as sulfur- and nitrogen-containing compounds in the product.

Further, in the process for producing a hydrocarbon and the process for producing a lube base oil of the present invention, the reaction product obtained by catalytic dewaxing using the hydroisomerization catalyst of the present invention can further be treated by, for example, hydrofinishing. Hydrofinishing can be typically carried out by contacting, in the presence of hydrogen, a hydrogenation catalyst supported on a metal (e.g., platinum supported on alumina), with the product to be finished. By performing such hydrofinishing, it is possible to improve the hue, oxidation stability, and the like of the reaction product obtained in the dewaxing step, thereby enhancing the product quality. The hydrofinishing may be carried out in reaction equipment separate from that of the dewaxing step; alternatively, a catalyst layer for hydrofinishing may be provided downstream the catalyst layer of the hydroisomerization catalyst of the present invention provided in the reactor for performing the dewaxing step, and the hydrofinishing may be performed subsequent to the dewaxing step.

It is noted that, in general, isomerization refers to a reaction whereby only the molecular structure changes without a change in the number of carbon atoms (the molecular weight), and cracking refers to a reaction that involves a decrease in the number of carbon atoms (molecular weight). In the catalytic dewaxing reaction utilizing the isomerization reaction, a certain degree of cracking of the hydrocarbon oil used as a stock and isomerized products may occur, as long as the number of carbon atoms (the molecular weight) of the product is maintained within a predetermined range that permits the formation of an intended base oil, and the cracked products may also be constituents of the base oil.

EXAMPLES

The present invention will be described in detail below, referring to examples; however, the invention is not limited to these examples.

[Production of Hydroisomerization Catalysts]

Example 1

Production of a Zeolite ZSM-22

A zeolite ZSM-22 (hereinafter sometimes referred to as the "ZSM-22") made of a crystalline aluminosilicate having a Si/Al ratio of 45 was produced by hydrothermal synthesis, according to the process described in *Chem. Eur. J*, 2007, vol. 13, page 1007, "Experimental Section", using the following procedure.

First, the following four types of aqueous solutions were prepared.
Solution A: A solution prepared by dissolving 1.94 g of potassium hydroxide in 6.75 mL of ion-exchange water.
Solution B: A solution prepared by dissolving 1.33 g of aluminum sulfate 18-hydrate in 5 mL of ion-exchange water.
Solution C: A solution prepared by diluting 4.18 g of 1,6-hexanediamine (an organic template) with 32.5 mL of ion-exchange water.
Solution D: A solution prepared by diluting 18 g of colloidal silica (Ludox AS-40 by Grace Davison) with 31 mL of ion-exchange water.

Next, Solution A was added to Solution B, and the mixture was stirred until the aluminum component completely dissolved. After Solution C was added to this mixed solution, the mixture of Solutions A, B, and C was poured into Solution D with vigorous stirring at room temperature. To the resulting mixture was further added, as a "seed crystal" that promotes crystallization, 0.25 g of a powder of ZSM-22 that had been separately synthesized, and had not been subjected to any special treatment after the synthesis, thereby giving a gel.

The gel obtained by the above procedure was transferred into a 120 mL internal volume stainless steel autoclave reactor, and the autoclave reactor was rotated at a rotational speed of about 60 rpm on a tumbling apparatus for 60 hours in an oven at 150° C., causing a hydrothermal synthesis reaction to take place. After the completion of the reaction, the reactor was opened after cooling, and dried overnight in a drier at 60° C., thereby giving ZSM-22 having a Si/Al ratio of 45.

<Ion exchange of Organic Template-Containing ZSM-22>

The ZSM-22 obtained above was subjected to ion-exchange treatment in an aqueous solution containing ammonium ions, according to the following procedure.

The ZSM-22 obtained above was taken in a flask, and 100 mL of 0.5 N-ammonium chloride aqueous solution per gram of the zeolite ZSM-22 was added thereto, and the mixture was heated under reflux for 6 hours. After cooling the heated mixture to room temperature, the supernatant was removed, and the crystalline aluminosilicate was washed with ion-exchange water. To the resulting product, the same amount of 0.5 N-ammonium chloride aqueous solution as above was added again, and the mixture was heated under reflux for 12 hours.

Subsequently, the solids were extracted by filtration, washed with ion-exchanged water, and dried overnight in a drier at 60° C., thereby giving ion-exchanged, $NH_4$-form ZSM-22. The ZSM-22 was an ion-exchanged zeolite containing an organic template.

<Addition of a Modifying Metal>

The $NH_4$-form ZSM-22 obtained above was calcined under an air stream for 3 hours at 400° C., giving an H-form ZSM-22. The H-form ZSM-22 was taken in a flask, and ion-exchanged at room temperature in a CsOH aqueous solution to give an amount of supported Cs such that the molar amount of cesium atoms was 0.05 times the molar amount of aluminum atoms ([Cs (mol)]/[Al (mol)]×100=5%).

Subsequently, the solids were extracted by filtration, washed with ion-exchanged water, and dried overnight in a drier at 60° C. This resulted in a Cs/H-form ZSM-22 modified with Cs by ion-exchange.

<Mixing of a Binder, Molding, and Calcination>

The Cs/H-form ZSM-22 obtained above was mixed with alumina, i.e., a binder, in a mass ratio of 7:3, a small amount of ion-exchange water was added thereto, and the mixture was kneaded. The resulting viscous fluid was loaded in an extruder and molded into a cylindrical molded product having a diameter of about 1.6 mm and a length of about 10 mm. This molded product was calcined under an air stream for 3 hours at 400° C., thereby giving molded and calcined support particles.

<Supporting of Platinum, and Calcination>

Tetraamminedichloroplatinum (II) ($Pt(NH_3)_4Cl_2$) was dissolved in an amount of ion-exchange water equivalent to the amount of water absorption of the support particles that had been previously measured, thus giving an impregnation solution. This solution was impregnated in the above-described support particles by incipient wetting, and supported on the support particles such that the amount of platinum was 0.3 mass % based on the mass of the zeolite ZSM-22. Next, the resulting impregnation product was dried overnight in a drier at 60° C., and then calcined under an air stream for 3 hours at 400° C., thereby giving Hydroisomerization Catalyst E-1.

Example 2

The same procedure as in Example 1 was performed, except that a MgOH aqueous solution was used instead of the CsOH aqueous solution, and that the H-form ZSM-22 was modified with Mg, thereby giving Hydroisomerization Catalyst E-2. Note that the amount of supported Mg [Mg (mol)]/[Al (mol)] was 0.05.

Example 3

The same procedure as in Example 1 was performed, except that a NaOH aqueous solution was used instead of the CsOH aqueous solution, and that the H-form ZSM-22 was modified with Na, thereby giving Hydroisomerization Catalyst E-3. Note that the amount of supported Na [Na (mol)]/[Al (mol)] was 0.05.

Example 4

The same procedure as in Example 1 was performed, except that a KOH aqueous solution was used instead of the CsOH aqueous solution, and that the H-form ZSM-22 was modified with K, thereby giving Hydroisomerization Catalyst E-4. Note that the amount of supported K [K (mol)]/[Al (mol)] was 0.05.

Example 5

The same procedure as in Example 1 was performed, except that a $Ca(NO_3)_2$ aqueous solution was used instead of the CsOH aqueous solution, and that the H-form ZSM-22 was modified with Ca, thereby giving Hydroisomerization Catalyst E-5. Note that the amount of supported Ca [Ca (mol)]/[Al (mol)] was 0.05.

Example 6

The same procedure as in Example 1 was performed, except that a $Ba(NO_3)_2$ aqueous solution was used instead of the CsOH aqueous solution, and that the H-form ZSM-22 was modified with Ba, thereby giving Hydroisomerization Catalyst E-6. Note that the amount of supported Ba [Ba (mol)]/[Al (mol)] was 0.05.

Example 7

Synthesis of a Zeolite ZSM-23

A crystalline aluminosilicate ZSM-23 (hereinafter sometimes referred to as the "ZSM-23") having a Si/Al ratio of 45 was produced by hydrothermal synthesis according to the process described in EXAMPLE 1 of U.S. Pat. No. 4,490,342.

First, Diquat-7 (N,N,N,N',N',N-hexamethyl-1,7-diaminoheptanedibromide), i.e., an organic template, was synthesized by partly modifying the process described in EXAMPLE A of the above-mentioned U.S. Pat. No. 4,490,342. Specifically, 50 g of 1,7-dibromoheptane and 100 mL of ethanol were mixed in a round bottom flask, 70 g of triethylamine (33 mass % ethanol solution) was added thereto with stirring, and the mixture was heated under reflux overnight. The reaction product was cooled to −21° C., and crystals were extracted by filtration. The crystals were washed with diethylether cooled to −21° C., and dried at room temperature, thereby giving intended Diquat-7 (a dibromide salt).

Using the Diquat-7 obtained above, the ZSM-23 was synthesized according to the following procedure.

First, the following two types of solutions were prepared.

Solution E: A solution prepared by diluting 15 g of colloidal silica (Ludox HS-40 by Grace Davison) with 31.6 mL of ion-exchange water.

Solution F: A solution prepared by thoroughly mixing 48.3 mL of ion-exchange water, 0.218 g of sodium aluminate, 1.22 g of sodium hydroxide, 0.9 g of sulfuric acid, and 2.74 g of the Diquat-7 salt.

Next, Solution F was poured into Solution E with stirring. The resulting gel was transferred into a 120 mL internal volume stainless steel autoclave reactor, and the reaction was allowed to proceed while rotating the autoclave reactor itself at a rotational speed of about 60 rpm for 72 hours in an oven at 160° C. After the completion of the reaction, the reactor was cooled, the produced solids were extracted by filtration, the solids were washed with ion-exchange water, and dried overnight in a drier at 60° C., thereby giving ZSM-23 having a Si/Al ratio of 45.

<Ion Exchange of Organic Template-Containing ZSM-23>

The same procedure as the ion exchange of ZSM-22 in Example 1 was performed, except that the organic template-containing ZSM-23 obtained above was used instead of the organic template-containing ZSM-22, thereby giving ion-exchanged $NH_4$-form ZSM-23.

<Addition of a Modifying Metal>

The same procedure as the treatment for the $NH_4$-form ZSM-22 in Example 1 was performed, thereby giving Cs/H-form ZSM-23 from the $NH_4$-form ZSM-23 obtained above.

<Mixing of a Binder, Molding, and Calcination>

Using the Cs/H-form ZSM-23 obtained above and alumina, i.e., a binder, the same procedure as in Example 1 was performed to give a molded product, which was then calcined, thereby giving molded and calcined support particles.

<Supporting of Platinum, and Calcination>

The same procedure as in Example 1 was performed, thereby supporting platinum on the support particles obtained above, and then calcination was performed, thereby giving Hydroisomerization Catalyst E-7.

Example 8

Synthesis of a Zeolite ZSM-48

An organic template-containing zeolite ZSM-48 (hereinafter sometimes referred to as the "ZSM-48") having a Si/Al ratio of 45 was synthesized based on *Applied Catalysis A: General* vol. 299 (2006) 167-174.

First, the following four types of reagents were prepared.
Reagent A: 2.97 g of sodium hydroxide.
Reagent B: 0.80 g of aluminum sulfate 18-hydrate.
Reagent C, 26.2 g of 1,6-hexanediamine (organic template).
Reagent D: 0.9 ml of a 98% sulfuric acid solution.
Reagent E: 75 g of a colloidal silica (Ludox AS-40 by Grace Davison) aqueous solution ($SiO_2$ concentration: 40%).

Next, Reagents A, B, C, D, and E mentioned above were added to 180 mg of ion-exchange water, and then completely dissolved by stirring for 2 hours at room temperature. The gel obtained after this procedure was transferred into a 100 mL internal volume stainless steel autoclave reactor, and the autoclave reactor was rotated at a rotational speed of about 60 rpm on a tumbling apparatus for 60 hours in an oven at 160° C., causing a hydrothermal synthesis reaction to take place. After the completion of the reaction, the reactor was opened after cooling, and dried overnight in a drier at 60° C., thereby giving ZSM-48 having a Si/Al ratio of 45.

<Ion Exchange of Organic Template-Containing ZSM-48>

The same procedure as the ion exchange of ZSM-22 in Example 1 was performed, except that the organic template-containing ZSM-48 obtained above was used instead of the organic template-containing ZSM-22, thereby giving ion-exchanged $NH_4$-form ZSM-48.

<Addition of a Modifying Metal>

The same procedure as the treatment for the $NH_4$-form ZSM-22 in Example 1 was performed, thereby giving Cs/H-form ZSM-48 from the $NH_4$-form ZSM-48 obtained above.

<Supporting of Platinum, and Calcination>

The same procedure as in Example 1 was performed, thereby supporting platinum on the support particles obtained above, and then calcination was performed, thereby giving Hydroisomerization Catalyst E-8.

Example 9

The same procedure as in Example 1 was performed, except that a ZSM-22 having a Si/Al ratio of 300 was used instead of the ZSM-22 having a Si/Al ratio of 45, thereby giving Hydroisomerization Catalyst E-9.

Example 10

The same procedure as in Example 1 was performed, except that a ZSM-22 having a Si/Al ratio of 10 was used instead of the ZSM-22 having a Si/Al ratio of 45, thereby giving Hydroisomerization Catalyst E-10.

Example 11

Subsequent to the <Ion exchange of Organic Template-Containing ZSM-22> in Example 1, the resulting $NH_4$-form ZSM-22 was mixed with alumina, i.e., a binder, in a mass ratio of 7:3, a small amount of ion-exchange water was added thereto, and the mixture was kneaded. The resulting viscous fluid was loaded in an extruder and molded into a cylindrical molded product having a diameter of about 1.6 mm and a length of about 10 mm. This molded product was calcined under an air stream for 3 hours at 400° C., thereby giving molded and calcined support particles.

<Addition of a Modifying Metal>

The support particles obtained above were taken in a flask, and ion-exchanged at room temperature in a CsOH aqueous solution to give an amount of supported Cs such that the molar amount of cesium atoms was 0.05 times the molar amount of aluminum atoms ([Cs (mol)]/[Al (mol)]×100=5%).

Subsequently, the solids were extracted by filtration, washed with ion-exchanged water, and dried overnight in a drier at 60° C. This resulted in Cs-modified support particles modified with Cs by ion-exchange.

<Supporting of Platinum, and Calcination>

Tetraamminedichloroplatinum (II) ($Pt(NH_3)_4Cl_2$) was dissolved in an amount of ion-exchange water equivalent to the amount of water absorption of the support particles that had been previously measured, thus giving an impregnation solution. This solution was impregnated in the above-described support particles by incipient wetting, and supported on the support particles such that the amount of platinum was 0.3 mass % based on the mass of the zeolite ZSM-22. Next, the resulting impregnation product was dried overnight in a drier at 60° C., and then calcined under an air stream for 3 hours at 400° C., thereby giving Hydroisomerization Catalyst E-11.

Example 12

Addition of a Modifying Metal

Subsequent to the <Ion exchange of Organic Template-Containing ZSM-22> in Example 1, the resulting $NH_4$-form ZSM-22 was taken in a flask, and ion-exchanged at room temperature in a CsOH aqueous solution to give an amount of supported Cs such that the molar amount of cesium atoms was 0.05 times the molar amount of aluminum atoms ([Cs (mol)]/[Al (mol)]×100=5%).

Subsequently, the solids were extracted by filtration, washed with ion-exchanged water, and dried overnight in a drier at 60° C. The dried solids were subsequently calcined under an air stream for 3 hours at 400° C., thereby giving a Cs/H-form ZSM-22 modified with Cs by ion-exchange.

<Mixing of a Binder, Molding, and Calcination>

The Cs/H-form ZSM-22 obtained above was mixed with alumina, i.e., a binder, in a mass ratio of 7:3, a small amount of ion-exchange water was added thereto, and the mixture was kneaded. The resulting viscous fluid was loaded in an extruder and molded into a cylindrical molded product having a diameter of about 1.6 mm and a length of about 10 mm. This molded product was calcined under an air stream for 3 hours at 400° C., thereby giving molded and calcined support particles.

<Supporting of Platinum, and Calcination>

Tetraamminedichloroplatinum (II) ($Pt(NH_3)_4Cl_2$) was dissolved in an amount of ion-exchange water equivalent to the amount of water absorption of the support particles that had been previously measured, thus giving an impregnation solution. This solution was impregnated in the above-described support particles by incipient wetting, and supported on the support particles such that the amount of platinum was 0.3 mass % based on the mass of the zeolite ZSM-22. Next, the resulting impregnation product was dried overnight in a drier at 60° C., and then calcined under an air stream for 3 hours at 400° C., thereby giving Hydroisomerization Catalyst E-12.

Comparative Example 1

The same procedure as in Example 1 was performed, except that the modifying metal Cs was not added, thereby giving Hydroisomerization Catalyst CE-1.

Comparative Example 2

The same procedure as in Example 1 was performed, except that all of the calcination temperatures were changed to 500° C., thereby giving Hydroisomerization Catalyst CE-2.

Comparative Example 3

The same procedure as in Example 1 was performed, except that all of the calcination temperatures were changed to 300° C., thereby giving Hydroisomerization Catalyst CE-3.

Comparative Example 4

Production of Catalyst SSZ-32

According to the process described in Japanese Patent Laid-Open No. 2006-523136, SSZ-32 was produced by hydrothermal synthesis, using the following procedure.

Sodium hydroxide, aluminium sulfate 18-hydrate, colloidal silica, isobutylamine, and an N-methyl-N-isopropyl-imidazolium cation were mixed to give the following molar ratios: $SiO_2/Al_2O_3=35$; the total molar amount of the isobutylamine and N-methyl-N'-isopropyl-imidazolium cation was 0.2 times the molar amount of $SiO_2$.

The gel obtained by the above procedure was transferred into a 100 mL internal volume stainless steel autoclave reactor, and the autoclave reactor was rotated at a rotational speed of about 60 rpm on a tumbling apparatus for 60 hours in an oven at 160° C., causing a hydrothermal synthesis reaction to take place. After the completion of the reaction, the reactor was opened after cooling, and dried overnight in a drier at 60° C., thereby giving SSZ-32 having a Si/Al ratio of 45.

<Mixing of a Binder, Molding, and Calcination>

A molded product was obtained from a mixture prepared by mixing the SSZ-32 obtained above with alumina, i.e., a reinforcing agent, in a mass ratio of 7:3, and then calcined, thereby giving molded and calcined particles. The calcination was performed for 3 hours at 400° C.

<Addition of a Modifying Metal>

The SSZ-32 obtained above was modified with Ca by ion exchange. Specifically, 10 g of the SSZ-32 obtained above was added to 30 cc of water heated to 70° C., and stirred for 10 minutes, after which 1 g of $Ca(OH)_2$ was added thereto.

<Supporting of Platinum, and Calcination>

The modified SSZ-32 obtained above was filtered, washed and dried, and then calcined to 900° F. (482° C.). Subsequently, platinum was incorporated by at least 5 hours of ion exchange at 160° F. (71° C.) using tetraamminedichloroplatinum (II) ($Pt(NH_3)_4Cl_2$), followed by filtration, washing, and calcination, thereby giving Hydroisomerization Catalyst CE-4.

Comparative Example 5

The same procedure as in Example 8 was performed, except that the modifying metal Cs was not added, thereby giving Hydroisomerization Catalyst CE-5.

[Evaluation of Isomerization Selectivities of the Catalysts]

For each of the catalysts obtained above in the Examples and Comparative Examples, the isomerization selectivity of the catalyst in the hydroisomerization reaction of a hydrocarbon was evaluated using the following test. It is noted that in the test, the isomerization selectivity was evaluated using n-hexadecane (nC16) as a hydrocarbon, by performing a hydroisomerization reaction in the following reactor under the following conditions, and by analyzing the resulting reaction product.

<Reactor>

A stainless steel-tube fixed bed microreactor having an inner diameter of 2.1 cm and a length of 30 cm was prepared as the reactor. This microreactor feeds oxygen gas and hydrogen gas for catalyst activation, nitrogen gas for purging, and normal hexadecane as a reaction feedstock by switching them with valves. The reaction was performed in a gaseous phase by loading 5 mg of each catalyst in the bottom of the stainless steel tube. The reaction product gas was collected with a pressure-controlled sampling valve provided downstream of the microreactor, and fed into a gas chromatograph (GC) equipped with a multi-capillary column using dimethylpolysiloxane as a stationary phase, and then analyzed.

<Reaction Conditions>

The isomerization reaction of normal hexadecane in the presence of hydrogen was performed under the following conditions:
Normal hexadecane feedstock: by Nacalai Tesque (purity: 99% or more)
Reaction pressure: 0.20 MPa
Hydrogen/normal decane ratio: 60 mol/mol
Reaction temperature: 280° C.

It is noted that in this test, the space velocity was adjusted such that the normal hexadecane conversion as determined by the following expression (1) was the same (95%), for the purpose of evaluating the isomerization selectivity of each catalyst relative to that of another catalyst.

Normal hexadecane ($n$C16) conversion (mass %)=
[100−the amount of normal hexadecane in the
reaction product (mass %)]  (1)

<Evaluation of Isomerization Selectivities>

The amount (mass %) of C16 isoparaffin in the reaction product was determined as the isomerization selectivity (%) of each hydroisomerization catalyst. The results are shown in Table 1.

TABLE 1

| | Hydroisomerization Catalyst | Zeolite | Si/Al (Molar Ratio) | Added Metal | nC16 Conversion | Isomerization Selectivity |
|---|---|---|---|---|---|---|
| Ex. 1 | E-1 | ZSM-22 | 45 | Cs | 95% | 90% |
| Ex. 2 | E-2 | ZSM-22 | 45 | Mg | 95% | 89% |
| Ex. 3 | E-3 | ZSM-22 | 45 | Na | 95% | 83% |
| Ex. 4 | E-4 | ZSM-22 | 45 | K | 95% | 83% |
| Ex. 5 | E-5 | ZSM-22 | 45 | Ca | 95% | 87% |
| Ex. 6 | E-6 | ZSM-22 | 45 | Ba | 95% | 84% |
| Ex. 7 | E-7 | ZSM-23 | 45 | Cs | 95% | 88% |
| Ex. 8 | E-8 | ZSM-48 | 45 | Cs | 95% | 88% |
| Ex. 9 | E-9 | ZSM-22 | 300 | Cs | 95% | 92% |

TABLE 1-continued

| | Hydroiso-merization Catalyst | Zeolite | Si/Al (Molar Ratio) | Added Metal | nC16 Con-version | Iso-merization Selectivity |
|---|---|---|---|---|---|---|
| Ex. 10 | E-10 | ZSM-22 | 10 | Cs | 95% | 85% |
| Ex. 11 | E-11 | ZSM-22 | 45 | Cs | 95% | 90% |
| Ex. 12 | E-12 | ZSM-22 | 45 | Cs | 95% | 90% |
| Comp. Ex. 1 | CE-1 | ZSM-22 | 45 | None | 95% | 82% |
| Comp. Ex. 2 | CE-2 | ZSM-22 | 45 | Cs | 95% | 70% |
| Comp. Ex. 3 | CE-3 | ZSM-22 | 45 | Cs | 95% | 78% |
| Comp. Ex. 4 | CE-4 | SSZ-32 | 45 | Ca | 95% | 79% |
| Comp. Ex. 5 | CE-5 | ZSM-48 | 45 | None | 95% | 80% |

Example 13 and Comparative Example 6

Using each of the molded catalysts obtained in Example 1 and Comparative Example 1, dewaxing of a wax, and separation and collection of a lube base oil fraction were performed (Example 13 and Comparative Example 6).

(Dewaxing of a Wax)

A stainless-steel reactor having an inner diameter of 15 mm and a length of 380 mm was loaded with 100 ml of each molded catalyst, and reduction treatment was performed for 12 hours under a hydrogen stream (the hydrogen partial pressure: 3 MPa) at a catalyst layer average temperature of 350° C. Subsequently, a petroleum-based wax as a feedstock (the distribution of the numbers of carbon atoms: C20 to C43; the composition is shown in FIG. 1) was passed at a reaction temperature of 200° C., a hydrogen partial pressure of 3 MPa, a LHSV of 2.0 and a hydrogen/oil ratio of 500 NL/L, and the dewaxing treatment by hydroisomerization reaction was initiated. After 72 hours of reaction, the reaction product was collected and analyzed. In FIG. 1, a represents the amounts of isoparaffins, and b represents the amounts of normal paraffins.

Subsequently, at the same hydrogen partial pressure, LHSV, and hydrogen/oil ratio, the reaction temperature was increased stepwise to about 350° C., thereby increasing the feedstock conversion. After the reaction at each reaction temperature was conducted for 72 hours and stabilized, each reaction product was collected and analyzed.

(Separation and Recovery of Lube Base Oil Fractions)

Based on the analysis results for reaction products, each of the reaction products obtained at a reaction temperature at which the normal paraffin conversion as defined by the expression (I) above was 100%, was fractionated according to the following procedure, and the lube base oil fractions described below were separated and recovered.

Each of the reaction products obtained at reaction temperature at which the normal paraffin conversion was 100%, was first fractionated into naphtha, kerosene and gas oil fractions, and heavy fractions. The heavy fractions were further fractionated into a lube base oil fraction in the boiling point range of 330 to 410° C. and having a kinematic viscosity at 100° C. of 2.7±0.1 cSt (hereinafter referred to as the "lube base oil fraction 1", which is a lube base oil corresponding to 70 Pale of Group III+), and into a lube base oil fraction in the boiling point range of 410 to 450° C. and having a kinematic viscosity at 100° C. of 4.0±0.1 cSt (hereinafter referred to as the "lube base oil fraction 2", which is a lube base oil corresponding to SAE-10 of Group III+). The lowest reaction temperature at which the lube base oil fraction 2 had a pour point of −22.5° C. or less and a viscosity index of 140 or more was defined as Tc (° C.). Table 2 shows the yields of the lube base oil fractions 1 and 2 at the reaction temperature Tc, as well as the properties of the lube base oil fraction 2 at the reaction temperature Tc.

TABLE 2

| | Hydro-isomer-ization Catalyst | Reaction Temperature Tc (° C.) | Yield (%) of Lube Base Oil Fractions at Reaction Temperature Tc | | Properties of Lube Base Oil Fraction 2 at Reaction Temperature Tc | |
|---|---|---|---|---|---|---|
| | | | Fraction 1 | Fraction 2 | Pour Point (° C.) | Viscosity Index |
| Ex. 13 | E-1 | 325 | 31 | 48 | −27.5 | 148 |
| Comp. Ex. 6 | CE-1 | 325 | 28 | 46 | −25.0 | 144 |

The invention claimed is:

1. A catalyst used for hydroisomerization of a hydrocarbon, comprising a support and at least one metal selected from the group consisting of elements belonging to Groups 8 to 10 of the periodic table, molybdenum, and tungsten, wherein
   the support comprises
   a calcined zeolite, which is modified with Cs,
   the calcined zeolite being prepared by calcining an ion-exchanged zeolite, that has not previously been heated at 350° C. or more, at a temperature within a range of 350 to 450° C., the ion-exchanged zeolite being obtained by ion exchange of an organic-template-containing zeolite, which comprises an organic template and has a 10-membered ring one-dimensional porous structure, in a solution containing ammonium ions and/or protons; and
   at least one inorganic oxide selected from the group consisting of alumina, silica, titania, boria, zirconia, magnesia, ceria, zinc oxide, phosphorus oxide, and a composite oxide containing a combination of at least two or more of these oxides.

2. The hydroisomerization catalyst according to claim 1, wherein the organic template-containing zeolite is at least one selected from the group consisting of a zeolite ZSM-22, a zeolite ZSM-23, and a zeolite ZSM-48.

3. The hydroisomerization catalyst according to claim 1, wherein the inorganic oxide is alumina.

4. The hydroisomerization catalyst according to claim 1, wherein the metal supported on the support is platinum and/or palladium.

5. The hydroisomerization catalyst according to claim 1, wherein a molar ratio of silicon atoms to aluminum atoms ([Si]/[Al]) in the organic template-containing zeolite is 10 to 400.

6. A method of dewaxing a hydrocarbon oil comprising contacting, in the presence of hydrogen, a hydrocarbon oil containing normal paraffins having 10 or more carbon atoms, with the hydroisomerization catalyst of claim 1, thereby converting a portion or all of the normal paraffins to isoparaffins.

7. The method according to claim 6, wherein the hydrocarbon oil is at least one selected from the group consisting of hydrocracked vacuum gas oils, hydrocracked atmospheric residual oils, hydrocracked vacuum residual oils, hydrodesulfurized vacuum gas oils, hydrodesulfurized atmospheric residual oils, hydrodesulfurized vacuum residual oils, slack waxes, dewaxed oils, paraffinic waxes, microcrystalline waxes, petrolatum, and Fischer-Tropsch synthesis waxes.

8. A process for producing a hydrocarbon comprising contacting, in the presence of hydrogen, a hydrocarbon feedstock containing normal paraffins having 10 or more carbon atoms, with the hydroisomerization catalyst of claim 1.

9. The process according to claim 8, wherein the hydrocarbon feedstock is at least one selected from the group consisting of hydrocracked vacuum gas oils, hydrocracked atmospheric residual oils, hydrocracked vacuum residual oils, hydrodesulfurized vacuum gas oils, hydrodesulfurized atmospheric residual oils, hydrodesulfurized vacuum residual oils, slack waxes, dewaxed oils, paraffinic waxes, microcrystalline waxes, petrolatum, and Fischer-Tropsch synthesis waxes.

10. A process for producing a lube base oil comprising contacting, in the presence of hydrogen, a hydrocarbon feedstock containing normal paraffins having 10 or more carbon atoms, with the hydroisomerization catalyst of claim 1, under conditions that give substantially 100 mass % conversion of the normal paraffins, as defined by the following expression (I):

$$\text{Normal paraffin conversion (\%)} = \left[1 - \frac{\left(\begin{array}{c}\text{Total mass of the normal paraffins}\\\text{having } Cn \text{ or more contained}\\\text{in the hydrocarbon oil after contacting}\end{array}\right)}{\left(\begin{array}{c}\text{Total mass of the normal paraffins}\\\text{having } Cn \text{ or more contained}\\\text{in the hydrocarbon oil before contacting}\end{array}\right)}\right] \times 100 \quad (I)$$

wherein $Cn$ represents a minimum number of carbon atoms of the normal paraffins having 10 or more carbon atoms contained in the hydrocarbon feedstock before contacting.

11. The process according to claim 10, wherein the hydrocarbon feedstock after being contacted with the hydroisomerization catalyst is further hydrofinished, and then distilled under vacuum.

* * * * *